United States Patent
Al-Matouq

(10) Patent No.: US 10,297,353 B1
(45) Date of Patent: May 21, 2019

(54) ESTIMATION OF GLUCOSE RATE OF APPEARANCE, ENDOGENOUS GLUCOSE PRODUCTION AND INSULIN DEPENDENT GLUCOSE UTILIZATION FROM CONTINUOUS GLUCOSE SENSORS AND SUBCUTANEOUS INSULIN DELIVER

(71) Applicant: Prince Sultan University, Riyadh (SA)

(72) Inventor: Ali Ahmed Al-Matouq, Riyadh (SA)

(73) Assignee: Prince Sultan University, Riyadh (SA)

( * ) Notice: Subject to any disclaimer, the term of this patent is extended or adjusted under 35 U.S.C. 154(b) by 0 days.

(21) Appl. No.: 15/974,451

(22) Filed: May 8, 2018

(51) Int. Cl.
*G16H 50/50* (2018.01)
*A61B 5/00* (2006.01)
*A61B 5/145* (2006.01)
*A61M 5/172* (2006.01)

(52) U.S. Cl.
CPC ......... *G16H 50/50* (2018.01); *A61B 5/14532* (2013.01); *A61B 5/4839* (2013.01); *A61B 5/0002* (2013.01); *A61B 5/7271* (2013.01); *A61M 5/1723* (2013.01); *A61M 2205/52* (2013.01)

(58) Field of Classification Search
CPC .. G16H 50/50; A61B 5/14532; A61B 5/4839; A61B 5/0002; A61B 5/7271; A61M 5/1723; A61M 2205/52
USPC .......... 340/573.1; 604/506; 600/365
See application file for complete search history.

(56) References Cited

U.S. PATENT DOCUMENTS

| | | | | |
|---|---|---|---|---|
| 2009/0006133 A1* | 1/2009 | Weinert | ............ | A61B 5/14532 705/3 |
| 2009/0054753 A1* | 2/2009 | Robinson | ........... | A61B 5/14503 600/365 |
| 2013/0158504 A1* | 6/2013 | Ruchti | ................ | A61M 5/1723 604/504 |
| 2015/0359966 A1* | 12/2015 | Day | ........................ | G16H 20/10 604/506 |
| 2016/0354543 A1* | 12/2016 | Cinar | .................. | A61M 5/1723 |

* cited by examiner

*Primary Examiner* — Jack K Wang
(74) *Attorney, Agent, or Firm* — Steven M. Shape; Dennemeyer & Associates, LLC

(57) ABSTRACT

Method and system for determining glucose flux profiles in plasma during meals using continuous glucose sensors and insulin delivery. A database of plausible glucose flux profiles is encoded in dictionaries using sparse dictionary learning. A constrained Lasso minimization problem is formed that integrates a transport model for a patient with the dictionaries for estimating the glucose fluxes. Meal carbohydrates consumed by a patient is incorporated in the minimization problem through convex constraints. The estimated glucose fluxes resulting from solving the constrained Lasso minimization problem are glucose rate of appearance from the intestine, endogenous glucose production from the liver and insulin dependent glucose utilization. A method for determining patient carbohydrate to insulin ratio at the time of the meal by calculating the area under the curve of the estimated insulin dependent glucose utilization.

16 Claims, 7 Drawing Sheets

ESTIMATION OF GLUCOSE RATE OF APPEARANCE, ENDOGENOUS GLUCOSE PRODUCTION AND INSULIN DEPENDENT GLUCOSE UTILIZATION FROM CONTINUOUS GLUCOSE SENSORS AND SUBCUTANEOUS INSULIN DELIVER

BACKGROUND OF THE INVENTION

Field of the Invention

The present disclosure relates to medical systems, more specifically, to a system for estimating glucose rate of appearance from the intestine, endogenous glucose production from the liver and insulin dependent glucose utilization.

Description of the Related Art

Continuous glucose sensors (hereafter CGS) can measure subcutaneous glucose concentrations in real time and has been successfully used in many recently developed Artificial Pancreas (hereafter AP) systems for regulating nighttime glucose [Doyle et al., 2014]. However, during meals, the situation gets more complicated as glucose traffic in the blood circulation becomes effected by the appearance of glucose from the intestine (due to the digestion of meal carbohydrates) and the disappearance of glucose due to insulin activation. Meal insulin when injected has the combined effect of stimulating glucose absorption by muscle and fat tissue and suppressing the liver from producing glycogen (which is usually produced at high levels while fasting). The premise is that for effective control of glucose during meals, it is important to measure the extent of glucose appearances and disappearances in plasma and not only subcutaneous glucose concentration.

Glucose rate of appearance from the intestine (hereafter GRA), is the glucose flux entering plasma originating from the digestion of meal carbohydrates (hereafter CHO). The flux profile for GRA will have a magnitude that depends on the size of the meal and a duration that may depend on meal composition [Home, 2015]. In healthy individuals, the pancreas beta cells will be partially stimulated to release insulin by the incretin hormones secreted by the intestine during meal digestion before reaching elevated plasma glucose levels [Home, 2015]. However, people with type 1 diabetes mellitus (hereafter T1DM) require external insulin to regulate plasma glucose during meals with a dosage that is calculated and injected without knowledge about the rate of glucose appearance from the intestine.

On the other hand, insulin dependent glucose utilization (hereafter U), is the absorption rate of glucose by muscles and adipose tissue due to insulin activation. This outlet flux has a profile with a magnitude that depends primarily on the amount of insulin delivered and patient or user specific insulin sensitivity at the time of the meal which can vary considerably depending on the condition of the patient or user and time of the day [Kudva et al., 2014]. Another important glucose flux entering the glucose concentration pool during meals is endogenous glucose production (hereafter EGP), which is normally suppressed by meal insulin. However, the extent of this suppression will also depend on patient specific insulin sensitivity at the time of the meal among other things. Other important, glucose fluxes are insulin independent glucose utilization by brain and erythrocytes (hereafter Uii), and renal excretion of glucose in urine (hereafter E), which occurs during relatively high glucose concentrations [Dalla Man et al., 2007].

Three of the mentioned flux disturbances, namely; GRA, EGP and U can be estimated in a clinical setting using multiple injected radioactive glucose tracers while a patient or user is undergoing a meal tolerance test (hereafter MTT). Such protocols, however, are expensive, invasive and can be subject to substantial errors as noted in [Rizza et al., 2016]. In the triple tracer technique, for example, two tracers are infused intravenously using infusion patterns that mimic EGP and GRA typical profiles while the third tracer is mixed with the meal. Five different plasma glucose measurements are then taken to trace back the different labelled and unlabelled glucose concentrations using the one compartment Steele's model [Steele, 1959] or the two compartment Radziuk/Mari model [Mari, 1992]. Attempts to reduce estimation errors of the glucose fluxes using these complex protocols was made in [Hovorka et al., 2007] under the maximum likelihood framework with a smoothness constraint on the unknown glucose fluxes and in [Haidar et al., 2012] under the Bayesian estimation framework.

A recent attempt for estimating GRA without the use of tracers and with minimal patient parameter identification was made in [Herrero et al., 2012]. Bergman's minimal model in [Bergman, 2003] was used assuming model parameters at average values except for patient specific insulin sensitivity which was found using numerical calculations. The technique, however, still requires intravenous measurements of both plasma glucose and plasma insulin and can only estimate GRA assuming no measurement noise present. In [Cameron et al., 2009], an algorithm was developed that uses the difference between predictions from a simple glucose-insulin model and CGS measurements to detect meal occurrences and to concurrently estimate GRA. In [Zecchin et al., 2012], a model for GRA in conjunction with a databased neural-network model was used to predict short-time glucose from CGS measurements. In [Eberle and Ament, 2012] observability of oral glucose intake from CGS measurements and insulin delivery measurements using an extension of Bergman's model was demonstrated. In [Visentin et al., 2016], identification of patient model parameters for the UVa Padova model developed in [Dalla Man et al., 2007] was demonstrated using plasma glucose and insulin concentration measurements for a number of patients or users. Maximum a posteriori estimation with Gaussian prior on model parameters was used. Such a technique, however, requires intravenous measurements of both plasma glucose and insulin that can be difficult to obtain. Moreover, the mentioned study was able to estimate GRA flux only, leaving out EGP and U to assume any shape. In [Turksoy et al., 2016], an unscented Kalman filter was used to estimate GRA using Bergman's minimal model for the detection of meal occurrences. In [Laleg-Kirati and Al-Matouq], an unknown input Kalman filter was used to estimate GRA using a model identified from triple tracer experimental data using CGS and insulin infusion measurements. However, none of the techniques presented so far can estimate GRA, EGP and U simultaneously using CGS and insulin infusion measurements.

There is currently no sensing device that measures GRA, EGP and U in a minimally invasive manner similar to measuring subcutaneous glucose using a CGS. It is desirable to estimate GRA, EGP and U using minimally invasive techniques by inferring it from CGS and insulin delivery measurements. Predicting the trajectory of glucose fluxes entering and leaving plasma during meals is important for diagnosis and treatment of type 1 diabetes mellitus (hereafter T1DM) and for drug development [Rizza et al., 2016].

SUMMARY OF THE INVENTION

The present disclosure relates to estimating GRA, EGP and U signals of a person during a meal by using (1) a single or a plurality of CGS sensors coupled to a patient; (2) a dynamic glucose/insulin model for the patient; (3) information indicating the time and amount of bolus and basal insulin injected to a person; (4) information indicating the time and amount of meal carbohydrates consumed by the patient during the same meal and (5) signal dictionaries (or basis vectors) that encode a database of plausible glucose flux profile signals using sparse encoding (dictionary learning [Mairal et al., 2009]) and (6) a convex optimization algorithm that processes the information from (1) to (5) through solving an optimization problem to find (1) an estimate of the signal for glucose rate of appearance GRA, (2) an estimate of the signal for endogenous glucose production EGP and (3) an estimate of the signal for insulin dependent glucose utilization U. The preferred embodiments of the present disclosure can be programmed on a microcontroller or a digital signal processor for implementation.

The profiles of glucose fluxes GRA, EGP and U during meals exhibit distinctive temporal features. Such temporal features can be exploited using sparse dictionary learning techniques, as described, for example in [Mairal et al., 2009], for finding a relatively small number of basis vectors (signal building blocks) that can sparsely (compactly) represent an available large database of plausible glucose flux profiles for many patients. The database of plausible glucose flux profiles can be obtained from, for example, historical data from previous meal dual/triple tracer tests; simulation experiments of glucose/insulin models; literature data and/or a combination of thereof as explained in the preferred embodiments of the present disclosure. The obtained sparse basis vectors, afterwards, are used to reconstruct the unknown glucose fluxes GRA, EGP and U from noisy CGS measurements and insulin delivery measurements for a patient during a meal while being consistent with a glucose/insulin transport model of the patient and with the meal information provided. This is done by casting the estimation problem into a constrained Lasso (least absolute shrinkage and selection operator) optimization problem [Hastie et al., 2015] as explained in the preferred embodiments of the present disclosure.

The advantages of the present system and method are the present disclosure requires only continuous glucose sensor measurements, insulin infusion recordings, meal information, patient model parameters, initial conditions and basis vectors that encode plausible glucose flux profiles to obtain plausible estimates of the glucose fluxes GRA, EGP and U during/after meals which can be considered a major paradigm shift over traditional techniques that require multiple radioactive tracers and multiple intravenous measurements in a clinical setting, as proposed for example in [Basu et al., 2003]. Such measurement protocols are expensive, invasive and can be subject to substantial errors as noted in [Rizza et al., 2016]. In addition, patient specific dictionaries (basis vectors) are not required to estimate the flux profiles; rather a single dictionary can be used that encodes a large set of plausible flux profiles. This will be demonstrated in the present disclosure. Consequently, this avoids having the need to estimate, for example, patient specific insulin sensitivity at the time of the meal or finding a parametric model that takes into account meal composition effects. Further, the estimation results can be found relatively fast using convex programming that is used to solve relatively small to medium size problems. Forth, the disclosure demonstrates good recovery results for low measurement sample rates (as low as 5 minutes per sample) even when noisy measurements and uncertain initial conditions are used as will be demonstrated in the preferred embodiments of the present disclosure. The system and method described and illustrated include the availability of (1) a large representative database of plausible glucose flux profiles to be encoded in a dictionary using sparse encoding [Mairal et al., 2009] and (2) the availability of patient specific parameters relevant to the transport model being used. One way to address these requirements is by using, for example, the (Food and Drug Administration) (hereafter FDA) approved UVa/Padova simulator developed in [Dalla Man et al., 2007] and [Dalla Man et al., 2014], which provides a library of parameter sets for different virtual patients and a simulation environment that can be used to construct a database of plausible glucose flux profile signals for GRA, EGP and U.

Still other objects and advantages of the disclosure described and shown in the specification and drawings.

BRIEF DESCRIPTION OF THE DRAWINGS

For a more complete understanding of the disclosure, reference is made to the following description and accompanying drawings, in which.

DETAILED DESCRIPTION OF THE PREFERRED EMBODIMENTS

The preferred embodiments of the present disclosure described herein relate to estimating the glucose fluxes GRA, EGP and U of a person using measurements obtained from a CGS coupled to a person in the presence of sensor noise, recordings of time and amount of insulin injected subcutaneously to the patient and information related to the amount of carbohydrates consumed during meals. The preferred embodiments will be disclosed with reference to specific examples to simplify discussion and should not be interpreted as a limitation in any respect.

The objective of this disclosure is to estimate the glucose flux disturbance signals for GRA (hereafter $u_{ra}(t)$), the signal for EGP, (hereafter $u_{egp}(t)$) and the signal for U, (hereafter $u_{ins}(t)$) during meals using noisy measurements of subcutaneous glucose and insulin delivery; a dynamic model of the patient; the amount of meal carbohydrates in the meal consumed; available glucose flux dictionaries that contain a set of basis vectors that can sparsely represent a large number of plausible glucose flux profiles during meals and a convex programming algorithm that can solve a convex optimization problem.

Figure 1:
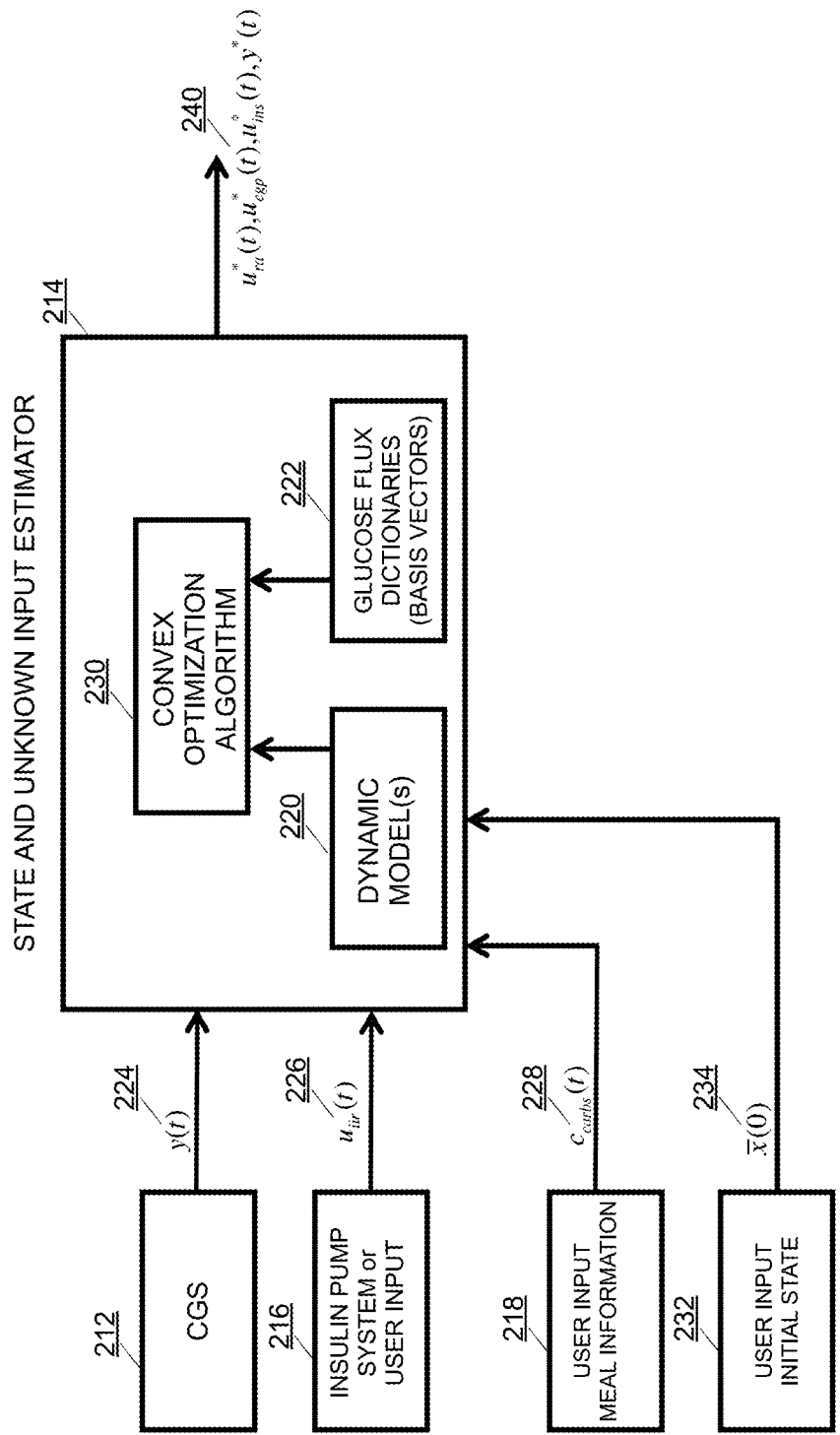
FIG. 1 is a block diagram for the GRA, EGP and U state and unknown input estimator.

FIG. 1 illustrates a block diagram showing a CGS device 212 which may be used to continuously measure the subcutaneous glucose concentration of the person according to an example of the disclosure. The CGS may be coupled to a person having diabetes (not shown). The CGS 212 transmits the noisy (unfiltered) measurements of subcutaneous glucose concentration 224 (denoted as y(t)) to the state and unknown input estimator module 214, hereafter state estimator. The noisy measurement signal y(t) 224 is interfaced to the state estimator system 214 via a wired or wireless communication link. The state estimator 214 will also take a noisy measurement signal $u_{iir}(t)$ 226 that measures the insulin infusion rate (both basal and bolus insulin) injected to the person subcutaneously which can come from an insulin pump system 216, hereafter IPS via a communication link or directly from the person or user as user input data to state estimator 214. State estimator 214 will also take a measurement signal $c_{carbs}(t)$ 228 that measures the amount of meal carbohydrates consumed by the patient obtained through a meal information device 218, or directly from the person as user input data (not shown) to state estimator 214. State estimator 214 will also take a measurement signal $\bar{x}_0$ 234 that measures the initial state vector obtained directly from the person as user input data 232 to state estimator 214. State estimator 214 includes a dynamic model 220 that captures the dynamic behavior of glucose and insulin concentration in plasma for the person whom the CGS device 212 and IPS device 216 is coupled to. State estimator 214 includes also glucose flux dictionaries 222 obtained from the dictionary learning process explained in the present disclosure. The state estimator 214 includes a convex optimization algorithm 230 that solves a convex optimization problem that incorporates the input CGS signal y(t) 224, the input insulin rate signal $u_{iir}(t)$ 226, the meal carbohydrate signal $c_{carbs}$ 228, the dynamic model(s) 220 and glucose flux dictionaries 222. The solution of the convex optimization problem will provide the estimated glucose flux signals 240 which include the signals $u_{ra}^*(t)$ that is indicative of the GRA signal $u_{ra}(t)$; $u_{egp}^*(t)$ that is indicative of the EGP signal $u_{egp}(t)$; $u_{ins}^*(t)$ that is indicative of the U signal $u_{ins}(t)$ and the filtered CGS signal $y^*(t)$ that is a filtered version of the noisy measurement signal y(t).

The unique utilization of glucose flux dictionaries 222 that contain basis vectors representing a sparse vector space of plausible glucose fluxes, enables the estimation of the glucose fluxes GRA, EGP and U using minimally invasive sensors while providing a solution that is relatively easy to implement. Moreover, the utilization of glucose flux dictionaries (basis vectors) helps to avoid estimating patient specific insulin sensitivity for stimulating glucose absorption by body tissue and parameters related to meal composition effects as explained later on in the preferred embodiments of the present disclosure.

The following notation is used in the present disclosure: $\mathbb{R}$ the set of real numbers, $\mathbb{R}_+$ represents the set of positive real numbers; $A \in \mathbb{R}^{n \times m}$ is an n×m matrix that belongs to the set of real n×m matrices $\mathbb{R}^{n \times m}$; $\|z\|_{l_i}$ is the $l_i$ norm of vector z and |z| represents the cardinality of vector z; i.e. the number of non-zero elements in the vector z.

The transport model for the glucose/insulin system of a patient developed in [Dalla Man et al., 2014] will be briefly described here as an example demonstrating the utilization of a transport model in the present disclosure and should not be interpreted as a limitation in any respect.

The glucose subsystem transport model used in the UVA/Padova simulator is given by the following mass balance equations [Dalla Man et al., 2014]:

$$\frac{dg_p}{dt} = u_{ra}(t) + u_{egp}(t) - u_{ii}(t) - u_e(t) - k_1 g_p(t) + k_2 g_t(t) \quad (1)$$

$$\frac{dg_t}{dt} = -u_{ins}(t) + k_1 g_p(t) - k_2 g_t(t)$$

$$\frac{dg_{sc}}{dt} = \frac{1}{\tau}(g - g_{sc})$$

$$g(t) = g_p(t)/v_g$$

$$g_p(0) = g_{pb}, g_t(0) = g_{tb}, g_{sc}(0) = g(0) = g_b = \frac{g_{pb}}{v_g}$$

where $g_p(t)$ (mg/kg) is mass of glucose in plasma and fast equilibrating tissue per kg of patient body weight; $g_t(t)$ (mg/kg) is mass of glucose in slowly equilibrating tissue per kg of patient body weight; g(t) is plasma glucose concentration in (mg/dl) and $g_{sc}(t)$ is subcutaneous glucose concentration in mg/dl. From the above equation, the glucose fluxes in units of mg per kg patient body weight per minute, (mg/kg·min) are the glucose rate of appearance from the intestine $u_{ra}(t)$, the endogenous glucose production from the liver $u_{egp}(t)$, the renal excretion of glucose in urine $u_e(t)$, the insulin independent glucose utilization by the brain and erythrocytes $u_{ii}(t)$ and the insulin dependent glucose utilization by muscle and adipose tissue $u_{ins}(t)$. Here, $v_g$ is the distribution volume of glucose in plasma in (dl/kg) and $k_1$ and $k_2$ in min$^{-1}$ are the diffusion rates for glucose between plasma and peripheral tissue and peripheral tissue to plasma respectively. The initial conditions for the states are given by the basal levels of plasma glucose $g_{pb}$ and tissue glucose $g_{tb}$ respectively. Finally, τ(min) is a time lag accounting for physiological and sensor delays. To simplify discussion, the assumption that $u_{ii}=f_{cns}=1$(mg/kg/min) and $u_e \approx 0$ will be used i.e. insulin independent glucose utilization is constant given by $f_{cns}$ and no renal excretion of glucose in urine is present (which usually becomes considerable at elevated levels of plasma glucose [Dalla Man et al., 2014]). However, these are not limiting assumptions as the estimation of $u_{ii}$ and $u_e$ can be carried out using the same technique for estimating $u_{ra}(t)$, $u_{egp}(t)$ and $u_{ins}(t)$.

An insulin kinetics model can be used in the disclosure to model the effect of insulin on endogenous glucose production. For example, insulin kinetics in [Dalla Man et al., 2014] is described using a two compartment model given as:

$$\frac{di_p}{dt} = -(m_2 + m_4)i_p(t) + m_1 i_l(t) + u_{ira}(t) \quad (2)$$

$$\frac{di_l}{dt} = m_2 i_p(t) - (m_1 + m_3)i_l(t)$$

$$i(t) = i_p(t)/v_i, \, i_p(0) = i_{pb}, \, i_l(0) = i_{lb}$$

where, $i_p(t)$, $i_l(t)$ (pmol/kg) are insulin masses in plasma and liver respectively; i(t) (pmol/l) is plasma insulin concentration; $u_{ira}$ (pmol/kg·min) is insulin rate of appearance in plasma; $v_i$ (l/kg) is the distribution volume of insulin; $m_1$, $m_2$ (min$^{-1}$) are the diffusion rates of insulin from liver to plasma and from plasma to liver respectively while $m_3$ and $m_4$ (min$^{-1}$) are rates of liver and peripheral insulin degradation respectively (assumed linear). The initial conditions for the two states are given by the basal levels of plasma insulin $i_{pb}$ and liver insulin $i_{lb}$ respectively. Insulin rate of appearance is described by the following two compartment model:

$$u_{ira} = k_{a1} i_{sc1}(t) + k_{a2} i_{sc2}(t) \quad (3)$$

$$\frac{di_{sc1}}{dt} = -(k_d + k_{a1}) i_{sc1}(t) + u_{iir}(t), \; i_{sc1}(0) = i_{sc1ss}$$

$$\frac{di_{sc2}}{dt} = k_d i_{sc1}(t) - k_{a2} i_{sc2}(t), \; i_{sc2}(0) = i_{sc2ss}$$

where, $i_{sc1}(t)$, $i_{sc2}(t)$ (pmol/kg) are insulin masses in the first and second subcutaneous compartments, $u_{iir}(t)$ (pmol/kg·min) is the subcutaneous insulin infusion rate while $k_{a1}$, $k_{a2}$ (min$^{-1}$) and $k_d$ (min$^{-1}$) are rate parameters.

The effect of glucose and insulin on endogenous glucose production can be described by the following model in [Dalla Man et al., 2014]:

$$u_{egp} = k_{p1} - k_{p2} g_p(t) - k_{p3} i_{d1}(t) \quad (4)$$

$$\frac{di_{d1}}{dt} = -k_i (i_{d1}(t) - i_{d2}(t))$$

$$\frac{di_{d2}}{dt} = -k_i (i_{d2}(t) - i(t))$$

$$i_{d1}(0) = i_{d2}(0) = i_{pb}/v_i$$

where $i_{d1}(t)$ (pmol/l) is called insulin action on glucose production; $i_{d2}(t)$ (pmol/l) is the delayed compartment for insulin action; $k_{p1}$ (mg/kg·min) is the extrapolated endogenous glucose production at zero glucose and insulin, $k_{p2}$ (min$^{-1}$) is liver glucose effectiveness, $k_{p3}$ (mg/kg·min per pmol/l) is a parameter governing amplitude of insulin action on the liver and $k_i$(min$^{-1}$) is a rate parameter accounting for delay between insulin signal and insulin action.

We will assume that initially no meal carbohydrates are on board; i.e. $u_{ra}(0)=0$. Furthermore, as in [Dalla Man et al., 2014], we will assume that $u_{ii}=u_{cns}=1$ mg/kg·min while $u_e \approx 0$ i.e. no renal excretion of glucose in urine. The above system of equations forms a linear time invariant system which can be represented in standard matrix state space form as follows:

$$\dot{x}(t) = A_c x(t) + B_{c,1} u(t) + B_{c,2} \tilde{u}(t)$$

$$y_c(t) = C_c x(t) \quad (5)$$

where, $$A_c := \begin{bmatrix} -(k_1+k_{p2}) & k_2 & 0 & 0 & 0 & 0 & 0 & -k_{p3} & 0 \\ k_1 & -k_2 & 0 & 0 & 0 & 0 & 0 & 0 & 0 \\ \frac{1}{\tau v_g} & 0 & -\frac{1}{\tau} & 0 & 0 & 0 & 0 & 0 & 0 \\ 0 & 0 & 0 & -(m_2+m_4) & m_1 & k_{a1} & k_{a2} & 0 & 0 \\ 0 & 0 & 0 & m_2 & -(m_1+m_3) & 0 & 0 & 0 & 0 \\ 0 & 0 & 0 & 0 & 0 & (-k_d+k_{a1}) & 0 & 0 & 0 \\ 0 & 0 & 0 & 0 & 0 & k_d & -k_{a2} & 0 & 0 \\ 0 & 0 & 0 & 0 & 0 & 0 & 0 & -k_i & k_i \\ 0 & 0 & 0 & \frac{k_i}{v_i} & 0 & 0 & 0 & 0 & -k_i \end{bmatrix}, \quad (6)$$

$$B_c := \begin{bmatrix} 1 & 0 & 1 & -1 & 0 \\ 0 & -1 & 0 & 0 & 0 \\ 0 & 0 & 0 & 0 & 0 \\ 0 & 0 & 0 & 0 & 0 \\ 0 & 0 & 0 & 0 & 0 \\ 0 & 0 & 0 & 0 & 1 \\ 0 & 0 & 0 & 0 & 0 \\ 0 & 0 & 0 & 0 & 0 \\ 0 & 0 & 0 & 0 & 0 \end{bmatrix}$$

$C_c := [0\ 0\ 1\ 0\ 0\ 0\ 0\ 0\ 0], B_{c,1} := B_c(:,1:2), B_{c,2} = B_c(:,3:5)$ and $$x(t) := [g_p(t), g_t(t), g_{sc}(t), i_p(t), i_l(t), i_{sc1}, i_{sc2}, i_{d1}, i_{d2}]^T$$

$$y(t) := g_{sc}(t), u(t) := [u_{ra}(t)\ u_{ins}(t)]^T$$

$$\tilde{u}(t) := [k_{p1}(t)\ f_{cns}\ u_{iir}(t)]^T$$

The matrices $A_c$, $B_{c,1}$, $B_{c,2}$ and $C_c$ are shown in (6) where $B_{c,1}$ is defined to be the first two columns of $B_c$ while $B_{c,2}$ as the last three columns of $B_c$. Here, subcutaneous glucose concentration $g_{sc}(t)$ was considered the output of the state space system which also represents an uncorrupted measurement of subcutaneous glucose. Matrix C can be redefined if more measurements are available, including, for example, multiple CGS measurements and/or plasma glucose and insulin concentration measurements.

Since CGS measurements measure subcutaneous glucose and are in discrete form, we may discretize (5) using, for example, zero order hold approximation [Rabbath and Lihevin, 2013], and add measurement noise to obtain the following discrete form of the model:

$$x_{k+1} = Ax_k + B_1 u_k + B_2 \tilde{u}_k, \quad x(0) = x_0$$

$$y_{k+1} = Cx_{k+1} + v_{k+1} \quad k = 0, \ldots N-1 \quad (7)$$

where, $x_k = x(kT_s) \in \mathbb{R}_+^9$, $y_k = y(kT_s) \in \mathbb{R}_+$, $u_k = u(kT_s) \in \mathbb{R}_+^2$, $\tilde{u}_k = \tilde{u}(kT_s) \in \mathbb{R}_+^3$, where N is the number of CGS measurements. The additional sequence $v_{k+1} \in \mathbb{R}$ in (9) is an unknown sequence and may account for any deviation from the linear relationship in (9), including, for example, measurement noise. CGS measurement noise has been studied in [Breton and Kovatchev, 2008] by comparing CGS recordings with plasma glucose concentration measurements and was modeled as a random sequence using a Johnson distribution with an autoregressive dynamic as follows [Breton and Kovatchev, 2008]:

$$v_k = \tilde{\zeta} + \tilde{\lambda} \sinh\left(\frac{e_k - \tilde{\gamma}}{\tilde{\delta}}\right), \quad (8)$$

$$e_{k+1} = \tilde{\kappa}(e_k + \rho_k), \quad e_1 = \rho_1,$$

$$\rho_k \sim \mathcal{N}(0,1), \quad k = 1, \ldots, N$$

where, $\tilde{\kappa}$ is called the autocorrelation coefficient, $\rho_k$ is a normally distributed zero mean unit covariance sequence and $\tilde{\zeta}$, $\tilde{\lambda}$, $\tilde{\gamma}$ and $\tilde{\delta}$ are parameters of the SU Johnson distribution.

Sparse vector spaces for GRA and U are incorporated in the estimation problem versus dynamic models describing GRA and U. Incorporating dynamic models for GRA, and U will entail significant parameter uncertainties and non-linearities which can influence estimation accuracy. More specifically, the length and shape of the profile for $u_{ra}(t)$ depends on meal composition which is not accounted for in [Dalla Man et al., 2014]. Moreover, the profile for $u_{ins}$ depends on insulin sensitivity, which can vary considerably within a patient and even during a single day as discussed in [Kudva et al., 2014] which is also not accounted for in [Dalla Man et al., 2014]. However, incorporating sparse vector spaces can help to account for model parameter uncertainties as will be demonstrated in the disclosure. In addition, incorporating sparse vector spaces in estimating the unknown glucose fluxes will transform the problem into a convex optimization problem that can be implemented on standalone microprocessors [Mattingley and Boyd, 2012].

Figure 2:
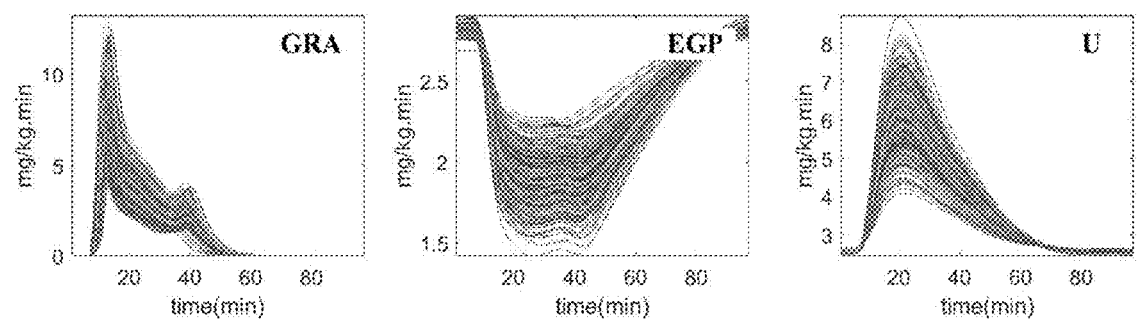
FIG. 2 plots demonstrating an example of a database glucose profile signals for GRA, EGP and U based on several simulation trials on the UVa/Padova simulator.

FIG. 2 illustrates plots for GRA, EGP and U verses time obtained from a large number of simulation trials of the UVA/Padova simulator [Dalla Man et al., 2007]. Each simulation trial was for a single meal scenario where a patient injects meal insulin at minute 29 and a meal is then consumed with a certain amount of meal carbohydrates starting from minute 30. The amount of meal carbohydrates, the duration of each meal and the patient parameters were varied at random in these simulation trials. The meal insulin dosage was calculated using an optimal bolus calculation method described in [Dalla Man et al., 2014]. The simulated profiles for GRA, EGP and U demonstrate some common patterns. For example, the simulated profiles for GRA shown in the first plot to the left of FIG. 2 demonstrate that GRA exhibits a distinctive jump at the start of the meal followed by a slow decay as compared to the profiles of EGP (middle plot in FIG. 2) and U (right plot in FIG. 2) that rise and fall at a slower rate during meals. On the other hand, the simulated profiles for EGP (middle plot in FIG. 2) show the effect of insulin in suppressing endogenous glucose production while the simulated profiles for U (right plot in FIG. 2) increases slowly and peaks sufficiently after the peak of GRA demonstrating the delayed effect of insulin on glucose absorption. Exploiting the distinctive signal patterns for glucose flux profiles during meals by first constructing a database of plausible glucose flux profile signals and then using dictionary learning techniques to construct sparse dictionaries (basis vectors) that can represent vector spaces of glucose fluxes is shown.

Figure 3:
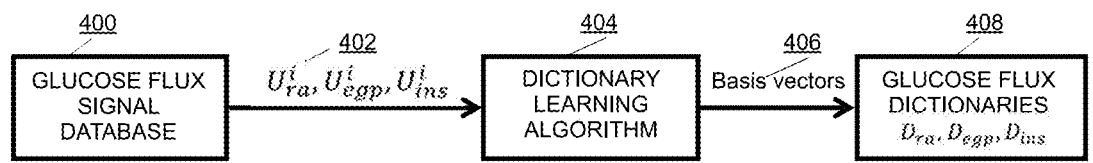
FIG. 3 is a block diagram for the dictionary learning process for developing the glucose flux dictionaries.

Referring to FIG. 3 is a block diagram that demonstrates the dictionary learning process of plausible glucose flux profile signals. A glucose flux signal database 400 contains plausible flux profiles for GRA (denoted $U_{ra}^i$), plausible flux profiles for EGP (denoted $U_{egp}^i$) and plausible flux profiles for U (denoted $U_{ins}^i$), where superscript i denotes the index of the signal. The database of plausible glucose flux profiles 400 can be obtained from, for example, historical recordings from previous dual/triple tracer tests; recordings obtained from simulation experiments; recordings obtain from the literature and/or a combination of thereof and/or other sources. The plausible flux profile signals shown in FIG. 2 are shown as an example of such database. Each single profile for each flux type in the plots will constitute the vectors $U_{ra}^i$, $U_{egp}^i$ and $U_{ins}^i$ corresponding to the ith profile of the glucose flux type GRA, EGP and U in the database, respectively. The plausible flux profile signals 402 are interfaced to a dictionary learning algorithm 404. Possible dictionary learning algorithms that can be used are, for example, the online dictionary learning algorithm explained in [Mairal et al., 2009] and/or the shift invariant dictionary learning algorithm explained in [Rusu et al., 2014]. These algorithms can be programmed, for example, on personnel computers or any computer processing device. The dictionary learning algorithm will produce basis vectors 406 (signal building blocks) from the database of the plausible glucose flux profiles 400. The basis vectors obtained from the dictionary learning algorithm 404 can be used to represent a sparse vector space for the glucose flux signals 402 coming from the database 400. Hence, any glucose profile in the database can be described using only a linear combination of a small number of basis vectors. Moreover, the same basis vectors can be also used to describe plausible glucose flux profiles that are not part of the training set since ideally the basis vectors constitute the building blocks for the space of all plausible glucose flux profiles. The basis vectors 406 for each glucose flux type obtained from the dictionary learning algorithm 404 will form the glucose flux dictionaries 408 that include a glucose flux dictionary for GRA (denoted $D_{ra}$), a glucose flux dictionary for EGP (denoted $D_{egp}$) and a glucose flux dictionary for U (denoted $D_{ins}$).

As an example and one embodiment of demonstrating the construction of glucose flux dictionaries of plausible glucose flux profile signals using dictionary learning techniques, we present the dictionary learning problem applied to a set of simulated flux profiles for GRA, EGP and U. The dictionary learning problem can be described as follows: given a set of $n_{ra}$ plausible glucose flux profile vectors for GRA denoted by $U_{ra}^1, \ldots, U_{ra}^{n_{ra}}$; $n_{egp}$ plausible glucose flux profile vectors for EGP denoted by $U_{egp}^1, \ldots, U_{egp}^{n_{egp}}$ and $n_{ins}$ plausible glucose flux profile vectors for U denoted by $U_{ins}^1, \ldots, U_{ins}^{n_{ins}}$ find dictionary matrices $D_{ra}$, $D_{egp}$ and $D_{ins}$ using the following minimization problem [Mairal et al., 2014]:

$$\min_{D_{ra} \in C, \alpha_{ra} \geq 0} \sum_{i=1}^{n_{ra}} \left( \frac{1}{2} \|U_{ra}^i - D_{ra}\alpha_{ra}^i\|_2^2 + \gamma \|\alpha_{ra}^i\|_1 \right) \quad (11)$$

$$\min_{D_{egp} \in C, \alpha_{egp} \geq 0} \sum_{i=1}^{n_{egp}} \left( \frac{1}{2} \|U_{egp}^i - D_{egp}\alpha_{egp}^i\|_2^2 + \gamma \|\alpha_{egp}^i\|_1 \right)$$

$$\min_{D_{ins} \in C, \alpha_{ins} \geq 0} \sum_{i=1}^{n_i} \left( \frac{1}{2} \|U_{ins}^i - D_{ins}\alpha_{ins}^i\|_2^2 + \gamma \|\alpha_{ins}^i\|_1 \right)$$

where, the set C is given by:

$$C \triangleq \{D_{ra} \in \mathbb{R}^{m \times p_{ra}}, D_{egp} \in \mathbb{R}^{m \times p_{egp}}, D_{ins} \in \mathbb{R}^{m \times p_{ins}} : \|d_j\|_2 \leq 1, \forall j\}$$

where, $d_j$ represents the jth column vector of $D_{ra}$, $D_{egp}$ and $D_{ins}$. The dictionaries $D_{ra}$, $D_{egp}$ and $D_{ins}$ are constrained to the set C to avoid having vectors with large numbers. For the case when $p_{ra}$, $p_{egp}$, $p_{ins} > N$ an over-complete dictionary with non-orthogonal vectors will result. Generally, it is desirable to reduce the number of basis vectors as much as possible to have a more compact representation, which can ultimately help in enhancing the recovery conditions [Hastie et al., 2015]. On the other hand, reducing the number of basis vectors, will increase the error between the training set vectors and the corresponding sparse representation. The tuning parameter y is selected for setting a desired sparsity level on $\alpha_{ra}$, $\alpha_{egp}$ and $\alpha_{ins}$ and can also reflect our confidence in the training set signals $U_{ra}^i$, $U_{egp}^i$ and $U_{ins}^i$. Problem (11) is a non-convex optimization problem that can be locally solved (i.e. for stationary points). Most algorithms use convex programming and alternate in solving for the dictionary and the codes while applying some update until convergence is obtained or maximum number of iterations is reached.

Figure 4:
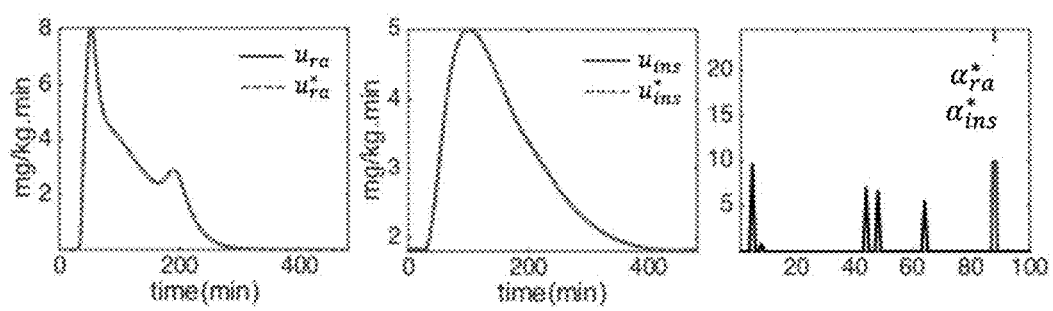
FIG. 4 is an example of typical glucose flux profiles for $u_{ra}$ and $u_{ins}$ during meals and the corresponding representation $u_{ra}{}^*$ and $u_{ins}{}^*$ using basis vectors $\alpha_{ra}{}^*$ and $\alpha_{ins}{}^*$ generated from the dictionary learning process.

The simulated meal profiles for GRA, EGP and U shown in FIG. 2 can be used as training vectors $U_{ra}^i$, $U_{egp}^i$ and $U_{ins}^i$ as an example demonstrating one embodiment of the present system and method. After obtaining the dictionaries $D_{ra}$, $D_{egp}$ and $D_{ins}$ using, for example, the dictionary learning process discussed above, the ith sparse codes for the ith glucose flux profile vectors $U_{ra}^i$, $U_{egp}^i$ and $U_{ins}^i$ in the database can be obtained from the following minimization problems:

$$\alpha_{ra}^{i*} = \arg\min_{\alpha_{ra}^i \geq 0} \frac{1}{2} \|U_{ra}^i - D_{ra}\alpha_{ra}^i\|_2^2 + \gamma \|\alpha_{ra}^i\|_1, \; i = 1, \ldots, n_{ra}$$

$$\alpha_{egp}^{i*} = \arg\min_{\alpha_{egp}^i \geq 0} \frac{1}{2} \|U_{egp}^i - D_{egp}\alpha_{egp}^i\|_2^2 + \gamma \|\alpha_{egp}^i\|_1, \; i = 1, \ldots, n_{ra}$$

$$\alpha_{ins}^{i*} = \arg\min_{\alpha_{ins}^i \geq 0} \frac{1}{2} \|U_{ins}^i - D_{ins}\alpha_{ins}^i\|_2^2 + \gamma \|\alpha_{ins}^i\|_1, \; i = 1, \ldots, n_{ins}$$

where, $\alpha_{ra}^{i*}$, $\alpha_{egp}^{i*}$ and $\alpha_{ins}^{i*}$ are called the sparse codes for the signals $U_{ra}^i$, $U_{egp}^i$ and $U_{ins}^i$, respectively. Consequently, the sparse representation of the ith glucose flux profile $U_{ra}^i$ for GRA in the database becomes $U_{ra}^{i*} = D_{ra}\alpha_{ra}^{i*}$ and the sparse representation of $U_{egp}^i$ in the database becomes $U_{egp}^{i*} = D_{egp}\alpha_{egp}^{i*}$ and the sparse representation of $U_{ins}^i$ in the database becomes $U_{ins}^{i*} = D_{ins}\alpha_{ins}^{i*}$. FIG. 4 gives an example of typical glucose flux profiles for $u_{ra}(t)$ and $u_{ins}(t)$ during meals and the corresponding representation $u_{ra}*(t)$ and $u_{ins}*(t)$ using basis vectors $\alpha_{ra}*$ and $\alpha_{ins}*$ generated from the dictionary learning process;

Referring to FIG. 1, the state estimator 214 is designed to estimate the glucose flux disturbances $u_{ra}$, $U_{egp}$ and $u_{ins}$ during a meal using (1) noisy CGS measurements 224; (2) basal and bolus insulin infusion rate recordings denoted by $u_{iir}$ 226; (3) patient model parameters for a glucose/insulin dynamic model 220; (4) an estimate of the initial state vector $\bar{x}_0$ 234 and (5) an estimate of the amount of meal carbohydrates in the meal being consumed $\bar{c}_{carbs}$(mg) 228 and (6) glucose flux dictionaries 222 (basis vectors) that encode plausible glucose flux profiles for $u_{ra}$ and $u_{ins}$ during meals. A constrained Lasso (least absolute shrinkage and selection operator [Hastie et al., 2015]) formulation will be used to estimate these fluxes which is described next demonstrating one of the preferred embodiments of the present system and methods.

We first expand the input output sequence relationship given by (9) in matrix form as follows:

$$Y_N = \Theta_N x_0 + T_{N_1} U_N + T_{N_2} \tilde{U}_N + V_N \quad (12)$$

$$\text{where, } Y_N := \begin{bmatrix} y_1 \\ \vdots \\ y_N \end{bmatrix}, U_N := \begin{bmatrix} u_0 \\ \vdots \\ u_{N-1} \end{bmatrix}, \tilde{U}_N := \begin{bmatrix} \tilde{u}_0 \\ \vdots \\ \tilde{u}_{N-1} \end{bmatrix}$$

$$V_N := \begin{bmatrix} v_1 \\ \vdots \\ v_N \end{bmatrix}, \Theta_N := \begin{bmatrix} CA \\ CA^2 \\ \vdots \\ CA^N \end{bmatrix}$$

$$T_{N_i} := \begin{bmatrix} CB_i & 0 & \cdots & 0 \\ CAB_i & CB_i & \ddots & 0 \\ \vdots & & \ddots & 0 \\ CA^{N-1}B_i & CA^{N-2}B_i & \cdots & CB_i \end{bmatrix}, i = 1, 2$$

We assume that the discrete state matrix A is marginally stable; i.e. |eig(A)|≤1. Marginal stability also requires that the geometric multiplicity of the eigenvalues on the unit circle to be not larger than 1. Furthermore, we assume that the matrix formed by the first n row blocks of $\Theta_N$, denoted by $\Theta_n$, is full column rank. These assumptions are needed so that the term $\Theta_N x_0$ is bounded; i.e. the sequence $CA^s x_0$ converges to a bounded solution as $s \to \infty$. The other part of the assumption is needed for guaranteeing a unique estimate of $x_0$ using the output sequence $y_k$ and both the input sequences $u_k$ and $\tilde{u}_k$ in finite time, which is known as the observability condition in system theory.

We define the glucose flux profile vectors as follows:

$$U_{ra} := [u_{ra}(0), \ldots, u_{ra}((N-1)T_s)]^T$$

$$U_{ins} := [u_{ins}(0), \ldots, u_{ins}((N-1)T_s)]^T$$

We assume that the glucose flux profiles $U_{ra}$ and $U_{ins}$ live inside a low dimensional vector space spanned by the column vectors of the dictionary matrices $D_{ra} \in \mathbb{R}^{N \times P_{ra}}$ and $D_{ins} \in \mathbb{R}^{N \times P_{ins}}$, respectively; i.e:

$$U_{ra}=D_{ra}\alpha_{ra}, \quad U_{ins}=D_{ins}\alpha_{ins}$$

where, $\alpha_{ra} \in \mathbb{R}^{P_{ra}}$ and $\alpha_{ins} \in \mathbb{R}^{P_{ins}}$ are sparse vectors with $|\alpha_{ra}|=s_{ra}$ and $|\alpha_{ins}|=s_{ins}$.

The construction of the sparse glucose flux dictionaries $D_{ra}$ and $D_{ins}$ was discussed in the previous section. Consequently, we may express the input vector $U_N$ as follows:

$$U_N = D_N \alpha \quad (13)$$

where, $$D_N := \begin{bmatrix} d_{ra,1}^T & 0 \\ 0 & d_{ins,1}^T \\ d_{ra,2}^T & 0 \\ 0 & d_{ins,2}^T \\ \vdots & \vdots \\ d_{ra,N}^T & 0 \\ 0 & d_{ins,N}^T \end{bmatrix}, \quad \alpha := \begin{bmatrix} \alpha_{ra} \\ \alpha_{ins} \end{bmatrix} \quad (14)$$

Here, $d_{ra,1}, d_{ra,2}, \ldots d_{ra,N} \in \mathbb{R}^{P_{ra}}$ are the N row vectors of $D_{ra}$, and $d_{ins,1}, d_{ins,2}, \ldots, d_{ins,N}$ are the N row vectors of $D_{ins}$, respectively. As a result, we can rewrite (12) as:

$$Y_N = \Theta_N x_0 + \Phi\alpha + T_{N_2}\tilde{U}_N + V_N$$

where, $\Phi = T_{N_1} D_N$ (15)

Using the set membership framework of estimation [Milanese and Vicino, 1991], we introduce additional a priori information on $x_0$ as an $l_2$ norm bound constraint given by:

$$\|x_0 - \bar{x}_0\|_2 \leq \varepsilon_{x_0} \quad (16)$$

where $\bar{x}_0$ is an estimate of the initial state vector and $\varepsilon_{x_0}$ is a known upper bound on the $l_2$ norm error for this estimate. Assuming steady state basal conditions are established at time zero, a plausible value for $\bar{x}_0$ could be: [Dalla Man et al., 2014]

$$\bar{x}_0 = [\bar{g}_{p,0}, \bar{g}_{t,0}, \bar{g}_{sc,0}, \bar{i}_{p,0}, \bar{i}_{l,0}, \bar{i}_{sc1,0}, \bar{i}_{sc2,0}, \bar{i}_{d1,0}, \bar{i}_{d2,0}]^T \quad (17)$$

$$\bar{g}_{p,0} = v_g\hat{g}_0, \quad \bar{g}_{t,0} = \frac{k_1}{k_2} v_g\hat{g}_0, \quad \bar{g}_{sc,0} = \hat{g}_0, \quad \bar{i}_{p,0} = i_{pb}, \quad \bar{i}_{l,0} = i_{lb}$$

$$\bar{i}_{sc1,0} = i_{sc1ss}, \quad \bar{i}_{sc2,0} = i_{sc2ss}, \quad \bar{i}_{d1,0} = \bar{i}_{d2,0} = i_{pb}/v_i$$

where, $\hat{g}_0$(mg/dl) is a plasma glucose concentration measurement taken at time zero. This can be obtained, for example, using a finger-prick blood glucose measurement device before the meal. For the other states, the basal values will be used in the absence of direct measurements. Here, we can also have individual $l_2$ error bounds for each element of $x_0$ if necessary to reflect the level of uncertainty for each initial state.

Additional a priori information can be incorporated related to the amount of meal carbohydrates. The area under the curve of $u_{ra}(t)$ represents the amount of glucose absorbed from meal carbohydrates, given by [Della Man et al., 2002]:

$$c_{bw}\int_{t=0}^{t=NT_s} u_{ra}(t)dt \approx c_{bw} \cdot \Sigma_{k=0}^{N} u_{ra}(kT_s)T_s = f c_{carbs} \quad (18)$$

where, f is the fraction of meal carbohydrates absorbed as glucose in plasma (glucose bioavailability), $c_{bw}$(kg) the patient body weight and $c_{carbs}$(mg) amount of meal carbohydrates consumed. In [Dalla Man et al., 2007], bioavailability was assumed fixed for all patients and given by f=0.9 (i.e. assuming no abnormalities in glucose absorption in the patient is present). In practice, meal carbohydrate measurement $c_{carbs}$ can be subject to uncertainties. We will assume that the uncertainty in $c_{carbs}$ can be represented also as an $l_2$ norm bound constraint on $c_{carbs}$ as follows:

$$\|c_{carbs} - \bar{c}_{carbs}\|_2 \leq \varepsilon_{carbs}$$

where $c_{carbs}$ is defined according to (18), $\bar{c}_{carbs}$ is an initial estimate of meal carbohydrates and $\varepsilon_{carbs}$ reflects the level of uncertainty in this measurement.

Hence, estimating the glucose fluxes amounts to the estimation of initial state vector $x_0$ and the sparse vector $\alpha$. Consequently, the following convex program is proposed for estimating $x_0$ and $\alpha$:

$$\alpha^*, x_0^* = \arg\min_{\alpha \geq 0, x_0 \geq 0} \|Y_N - \Theta_N x_0 - T_{N_2}\tilde{U}_N - \Phi\alpha\|_2^2 + \lambda\|\alpha\|_1$$

subject to:

$$\|x_0 - \bar{x}_0\|_2 \leq \varepsilon_{x_0}, \quad \|c_{carbs} - \bar{c}_{carbs}\|_2 \leq \varepsilon_{carbs}$$

$$D_{ra}\alpha_{ra} \geq 0, \quad D_{ins}\alpha_{ins} \geq 0$$

$$\Phi = T_{N_1} D_N, \quad c_{carbs} = c_{bw} \cdot f \Sigma_{k=0}^{N} d_{ra,k}^T \alpha_{ra} T_s, \quad f=0.9 \quad (19)$$

We mention the following related to the proposed convex program:

1. The $l_2$ norm term in the minimization ensures that the estimated vectors $x_0^*$ and $\alpha^*$ are consistent with the noisy CGS measurements in the least squares sense.
2. The $l_1$ norm term in the minimization ensures that the estimated vector $\alpha^*$ is sparse following our previous assumptions mentioned in the present disclosure.
3. Using the set membership framework of estimation [Milanese and Vicino, 1991], the $l_2$ norm bound constraints on $x_0$ and $c_{carbs}$ will limit the solution space of $x_0$ and $c_{carbs}$ to the $l_2$ norm balls defined by the centers $\bar{x}_0, \bar{c}_{carbs}$ and radius $\varepsilon_{x_0}, \varepsilon_{carbs}$, respectively.
4. Finally, the positivity constraint $\alpha \geq 0$ is imposed if non-negative sparse encoding is used, which is the case in our study as explained in the next section. Non-negative sparse encoding is used to make the value of $\alpha$ more interpretable.

In addition, the above formulation can be related to non-negative Lasso estimation that is known for its robustness to nonlinear distortion as studied in [Itoh et al., 2017]. A suitable value for the parameter $\lambda$ is found by repeated solution of (19) over a range of values for $\lambda$, as typically done in Lasso estimation [Hastie et al., 2015]. Finally we mention that the convex program (19) can be solved using, for example, interior point solvers as discussed, for example, in [Boyd and Vandenberghe, 2004] and can also be implemented in stand-alone microprocessors as explained, for example, in [Mattingley and Boyd, 2012].

After solving (19), the glucose flux profiles can then be found from the individual flux dictionaries as follows:

$$\begin{bmatrix} U_{ra}^* \\ U_{ins}^* \end{bmatrix} = \begin{bmatrix} D_{ra} & 0 \\ 0 & D_{ins} \end{bmatrix} \alpha^* \quad (20)$$

If desired, estimates of the unknown state sequence $x_k$ for $k=1, \ldots, N$ can also be found by solving the following recursion:

$$x_k^* = A^k x_0^* + \Sigma_{j=0}^{k-1} A^{k-j-1}(B_1 u_j^* + B_2 \tilde{u}_j), \quad k=1, \ldots N \tag{21}$$

where $u_j^* = [u_{ra}^*(T_s j), u_{ins}^*(T_s j)]$ $[d_{ra,j}^T \alpha_{ra}^*, d_{ins,j}^T \alpha_{ins}^*]$. Finally, estimation of the sequence $u_{egp}(kT_s)$ is found from the following recursion:

$$u_{egp}(kT_s)^* = k_{p1} - k_{p2} x_{k,1}^* - k_{p3} x_{k,2}^*, \quad k=1, \ldots N \tag{22}$$

Estimation of patient carbohydrate to insulin ratio.

Clinicians define the carbohydrate to insulin ratio as 500 divided by the total daily insulin dose (basal+bolus) [Kawamura, 2007]. This is considered to represent the amount of carbohydrates (measured in grams) that will be covered by one unit of rapid-acting insulin. Other rules make use of glycemic and food diary and are more suitable for children with large CIR variability [Kawamura, 2007]. In [Dalla Man et al., 2014], the definition of CIR was based on an optimal insulin dosage that ensures normal levels of blood glucose after a meal. A relevant measure for calculating patient CIR for a certain meal is by accounting for the glucose that has been disposed during the meal which can be calculated using the following equation:

$$c_{cir}^* = \frac{c_{bw} f}{c_{bolus}} \sum_{k=0}^{N} u_{ins}^*(kT_s) \cdot T_s \tag{23}$$

where, $c_{cir}^*$ (g/IU) is the meal CIR value using the proposed calculation, $c_{bolus}$ (IU) is the total amount basal and bolus insulin units delivered to the patient and $$f^* = \frac{c_{bw}}{c_{carbs}} \sum_{k=0}^{N} d_{ra,k}^T \alpha_{ra}^* T_s$$

is the estimated bioavailability.

Estimation of Patient Model Parameters

Techniques for identifying patient model parameters for the UVa Padova model are described in [Dalla Man et al., 2007] using triple tracer experimental data. Dual/triple tracer protocol for measuring glucose fluxes is described in [Basu et~al., 2003] and [Rizza et~al., 2016]. The above example, therefore, assumes that patient model parameters relevant to the glucose subsystem in (1), the insulin subsystem in (2) and the endogenous glucose production subsystem in (3) and (4) remain the same with possibly negligible changes in their values. As another approximate patient parameter estimation technique, the disclosure can make use of model parameter libraries as provided, for example in [Dalla Man et al., 2014]. In this case, a simple search technique can be used that will require fixing the tuning parameter $\lambda$ to a value that provides acceptable estimates and solving (19) repeatedly for all patient parameter sets in library of patient parameter sets until the lowest value of the objective in (19) is found.

For the case when identification of patient model parameters is difficult, or patient model parameters undergo significant changes, below is another example demonstrating another preferred embodiment of the present disclosed method and system that reduces the number of patient parameters required.

Estimation of Glucose Fluxes from CGS Measurements Assuming a Simple Model

As another example demonstrating one of the preferred embodiments of the present disclosure is when most of the patient model parameters relevant to glucose/insulin dynamics, as described earlier, are unknown. The method will require the use of an additional glucose flux dictionary for EGP, given earlier by $D_{egp}$ and additional a priori information in the form of patient carbohydrate to insulin ratio $c_{cir}$ and the initial value of the glucose flux $U_{egp}$. In the example below, only patient parameters $k_1$, $k_2$, $v_g$ and $\tau$ relevant to the glucose subsystem described in (1) will be assumed known for the patient. This is similar to the approach used in gold standard triple tracer technique described in [Basu et al., 2003] where patient parameters $k_1$, $k_2$ and $v_g$ relevant to the two compartment Radziuk/Mari model [Mari, 1992] were assumed fixed for all patients.

The glucose subsystem model equations given above in (1) can be written in state space form after redefining the state variable $x(t)$, the input vectors $u(t)$, $\tilde{u}(t)$ and matrices $A_c$, $B_{c,1}$, $B_{c,2}$, $C$ as follows:

$$\dot{x}(t) = A_c x(t) + B_{c,1} u(t) + B_{c,2} \tilde{u}(t)$$

$$y_c(t) = C_c x(t) \tag{24}$$

where the variables and matrices are now redefined to be as follows:

$$x(t) = [g_p(t) g_t(t) g_{sc}(t)]^T, \quad y_c(t) = g_{sc}(t), \tag{25}$$

$$u(t) = [u_{ra}(t), u_{egp}(t), u_{ins}(t)]^T$$

$$A_c = \begin{bmatrix} -k_1 & k_2 & 0 \\ k_1 & -k_2 & 0 \\ \frac{1}{\tau v_G} & 0 & \frac{1}{\tau} \end{bmatrix}, \quad B_{c,1} := \begin{bmatrix} 1 & 1 & 0 \\ 0 & 0 & -1 \\ 0 & 0 & 0 \end{bmatrix},$$

$$B_{c,2} := \begin{bmatrix} -1 \\ 0 \\ 0 \end{bmatrix}, \quad C_c = [0, 0, 1]$$

Consequently, we may discretize the continuous time state space model (24) using, for example, zero order hold approximation and add measurement noise to the discrete measurement signal $y_c(kT_s)$ as shown previously in the present disclosure to obtain the following discrete time state space system description:

$$x_{k+1} = A x_k + B_1 u_k + B_2 \tilde{u}_k, \quad x(0) = x_0$$

$$y_{k+1} = C x_{k+1} + v_{k+1} \quad k=0, \ldots N-1 \tag{26}$$

where, $x_k = x(kT_s) \in \mathbb{R}_+^3$, $y_k = y(kT_s) \in \mathbb{R}_+$, $u_k = u(kT_s) \in \mathbb{R}_+^3$, $\tilde{u}_k = \tilde{u}(kT_s) \in \mathbb{R}_+$, and N is the number of CGS measurements, as before. The additional sequence $v_k \in \mathbb{R}$ in (9) is an unknown sequence and may account for any deviation from the linear relationship in (26), as explained earlier, including, for example, measurement noise. CGS measurement noise has been studied in [Breton and Kovatchev, 2008] by comparing CGS recordings with plasma glucose concentration measurements and was modeled as a random sequence using a Johnson distribution with an autoregressive dynamic as described earlier in (10).

Next we define $Y_N$, $\Theta_N$, $T_{N_1}$ and $T_{N_2}$ as follows:

$$\text{where, } Y_N := \begin{bmatrix} y_1 \\ \vdots \\ y_N \end{bmatrix}, \quad U_N := \begin{bmatrix} u_0 \\ \vdots \\ u_{N-1} \end{bmatrix},$$

-continued $$\tilde{U}_N := \begin{bmatrix} \tilde{u}_0 \\ \vdots \\ \tilde{u}_{N-1} \end{bmatrix}, V_N := \begin{bmatrix} v_1 \\ \vdots \\ v_N \end{bmatrix}, \Theta_N := \begin{bmatrix} CA \\ CA^2 \\ \vdots \\ CA^N \end{bmatrix}$$

$$T_{N_i} := \begin{bmatrix} CB_i & 0 & \ldots & 0 \\ CAB_i & CB_i & \ddots & 0 \\ \vdots & & \ddots & 0 \\ CA^{N-1}B_i & CA^{N-2}B_i & \ldots & CB_i \end{bmatrix}, i = 1, 2$$

We also define the glucose flux profile vector for EGP as:

$$U_{egp} := [u_{egp}(0), \ldots, u_{egp}((N-1)T_s)]^T$$

We assume that the true glucose flux profile vector signals $U_{ra}$, $U_{egp}$, and $U_{ins}$ satisfy the following:

$$U_{ra} = D_{ra}\alpha_{ra}, \; U_{egp} = D_{egp}\alpha_{egp}, \; U_{ins} = D_{ins}\alpha_{ins}$$

where, $\alpha_{ra} \in \mathbb{R}^{P_{ra}}$, $\alpha_{egp} \in \mathbb{R}^{P_{egp}}$, $\alpha_{ins} \in \mathbb{R}^{P_{ins}}$ are sparse vectors with cardinality $s_{ra}$, $s_{egp}$ and $s_{ins}$ respectively. Consequently, using the row vectors of the glucose flux dictionaries, we may express the input vector $U_N$ as:

$$U_N = D_N \alpha \quad (27)$$

where, $$D_N := \begin{bmatrix} d_{ra,1}^T & 0 & 0 \\ 0 & d_{egp,1}^T & 0 \\ 0 & 0 & d_{ins,1}^T \\ d_{ra,2}^T & 0 & 0 \\ 0 & d_{egp,2}^T & 0 \\ 0 & 0 & d_{ins,2}^T \\ \vdots & \vdots & \vdots \\ d_{ra,N}^T & 0 & 0 \\ 0 & d_{egp,N}^T & 0 \\ 0 & 0 & d_{ins,N}^T \end{bmatrix}, \alpha := \begin{bmatrix} \alpha_{ra} \\ \alpha_{egp} \\ \alpha_{ins} \end{bmatrix} \quad (28)$$

where $d_{ra,1}, d_{ra,2}, \ldots d_{ra,N} \in \mathbb{R}^{P_{ra}}$ are the N row vectors of $D_{ra}$, $d_{egp,1}, d_{egp,2}, \ldots d_{egp,N}$ are the N vectors of $D_{egp}$ and $d_{ins,1}, d_{ins,2}, \ldots d_{ins,N}$ are the N vectors of $D_{ins}$ respectively. Hence, we may write as before the following matrix equation:

$$Y_N = \Theta_N x_0 + \Phi\alpha + T_{N_2}\tilde{U}_N + V_N$$

where, $\Phi = T_{N_1} D_N$

The estimation problem is now viewed as a sparse estimation problem where $Y_N$ is the noisy measurement vector; $T_{N_1} \in \mathbb{R}^{N \times 3N}$ the measurement matrix and $D_N \in \mathbb{R}^{3N \times p}$ the sparse dictionary for the unknown sparse vector $\alpha \in \mathbb{R}^P$, where $p = p_{ra} + p_{egp} + p_{ins}$.

Assuming steady state basal conditions are established at time zero, the following estimate of the initial state $x(0)$ may be used:

$$\bar{x}_0 = [\bar{g}_{p,0}, \bar{g}_{t,0}, \bar{g}_{sc,0}]^T$$

$$\bar{g}_{p,0} = v_g \hat{g}_0, \; \bar{g}_{t,0} = \frac{k_1}{k_2} v_g \hat{g}_0, \; \bar{g}_{sc,0} = \hat{g}_0 \quad (29)$$

In the absence of insulin information, additional a priori information is needed in the form carbohydrate to insulin ratio of the patient. This initial information can be described as a convex constraint as follows:

$$\|c_{cir} - \bar{c}_{cir}\| \leq \varepsilon_{cir} \quad (30)$$

$$c_{cir} = \frac{c_{bw}\bar{f}}{c_{bolus}} \sum_{k=0}^{N} u_{ins}(kT_s) \cdot T_s$$

where, $\bar{c}_{cir}$ is an estimate of the patient's carbohydrate to insulin ratio; $\bar{f}$ is an estimate of patient bioavailability; $\varepsilon_{cir}$ is a known lower bound on the $l_2$ norm error $\|c_{cir} - \bar{c}_{cir}\|$. Here, $c_{bolus}$ (IU) is the total amount of basal and bolus insulin units delivered to the patient which is assumed known. Such information can be obtained as user input data or from insulin infusion devices automatically via a communication link as described earlier.

Consequently, the following convex program is used to find estimates of GRA, EGP and U profiles during meals:

$$\alpha^*, x_0^* = \underset{\alpha, x_0}{\operatorname{argmin}} \|Y_N - \Theta_N x_0 - T_{N_2}\tilde{U}_N - \Phi\alpha\|_2^2 + \lambda\|\alpha\|_1 \quad (31)$$

$$\|x_0 - \bar{x}_0\|_2 \leq \varepsilon_{x_0}, \; \|c_{carbs} - \bar{c}_{carbs}\|_2 \leq \varepsilon_{carbs}$$

$$\|u_{egp}(0) - \bar{u}_{egp}(0)\| \leq \varepsilon_{egp}, \; \|c_{carbs} - \bar{c}_{carbs}\| \leq \varepsilon_{carbs}$$

$$D_{ra}\alpha_{ra} \geq 0, \; D_{egp}\alpha_{egp} \geq 0, \; D_{ins}\alpha_{ins} \geq 0$$

$$\Phi = T_{N_1} D_N, \; c_{carbs} = \frac{c_{bw}}{f} \sum_{k=0}^{N} d_{ra,k}^T \alpha_{ra} T_s, \; f = 0.9$$

where, $\alpha^*$ and $x_0^*$ are the optimal values for $\alpha$ and $x_0$ respectively. Here, $\bar{u}_{egp}(0)$ is an estimate of the initial value of the EGP flux and $\varepsilon_{egp}$ is a known lower bound on the $l_2$ norm error $\|u_{egp}(0) - \bar{u}_{egp}(0)\|$. After solving (31), the glucose flux profiles can then be found from the individual flux dictionaries as follows:

$$\begin{bmatrix} U_{ra}^* \\ U_{egp}^* \\ U_{ins}^* \end{bmatrix} = \begin{bmatrix} D_{ra} & 0 & 0 \\ 0 & D_{egp} & 0 \\ 0 & 0 & D_{ins} \end{bmatrix} \alpha^*$$

Estimates of the unknown state sequence $x_k$ for $k = 1, \ldots, N$ can also be found by solving the recursion appearing in equation (21) as before.

Simulation Examples

Several simulation examples will be given to demonstrate examples of the present disclosure. This will be done using UVA/Padova simulator discussed in [Dalla Man et al., 2014]. The first set of experiments validate performance using noisy simulation data that emulate meal tolerance test conditions (i.e. one meal insulin and one meal stage) while assuming perfect and imprecise knowledge of patient parameters. The second set of simulation experiments validate performance assuming imprecise knowledge of patient model parameters relevant to the glucose subsystem model given in (1) only.

Experiment I: Meal Tolerance Test Conditions with Complete Glucose/Insulin Model In the following experiment, two simulation trials are conducted using the UVa/Padova simulator [Dalla Man et al., 2014] demonstrating the present disclosure. Three in-silico patients named as the average adolescent, average adult and average child patient are specified by the UVa/Padova simulator were simulated. The specific patient parameters used for the transport model for the glucose subsystem appearing in (1), the plasma insulin subsystem appearing in (2), the subcutaneous insulin subsystem appearing in (3) and the endogenous glucose production subsystem appearing in (4) are shown in Table 1.

TABLE 1

Patient parameters for average adolescent, average adult and average child in-silico patients [Dalla Man et al., 2007]

| Patient/Param. | avg. adolescent | avg. adult | avg. child |
|---|---|---|---|
| $k_1(\text{min}^{-1})$ | 0.0870 | 0.0731 | 0.0746 |
| $k_2(\text{min}^{-1})$ | 0.0902 | 0.1077 | 0.1050 |
| $v_g(\text{dl/kg})$ | 1.8354 | 1.8480 | 1.8313 |
| $m_1(\text{min}^{-1})$ | 0.2135 | 0.1850 | 0.1889 |
| $m_2(\text{min}^{-1})$ | 0.3026 | 0.3130 | 0.2648 |
| $m_3(\text{min}^{-1})$ | 0.3202 | 0.2775 | 0.2833 |
| $m_4(\text{min}^{-1})$ | 0.1211 | 0.1252 | 0.1059 |
| $v_i(\text{l/kg})$ | 0.0503 | 0.0511 | 0.0480 |
| $k_{a1}(\text{min}^{-1})$ | 0.0038 | 0.0038 | 0.0043 |
| $k_{a2}(\text{min}^{-1})$ | 0.0176 | 0.0177 | 0.0197 |
| $k_d(\text{min}^{-1})$ | 0.0168 | 0.0162 | 0.0168 |
| $k_{p1}(\text{mg/kg} \cdot \text{min})$ | 5.4807 | 4.9866 | 5.0789 |
| $k_{p2}(\text{min}^{-1})$ | 0.0048 | 0.0055 | 0.0049 |
| $k_{p3}(\text{mg} \cdot \text{l/kg} \cdot \text{min} \cdot \text{pmol})$ | 0.0136 | 0.0105 | 0.0098 |
| $k_i(\text{min}^{-1})$ | 0.0100 | 0.0109 | 0.0101 |
| bw(kg) | 48.77 | 69.6 | 29.97 |
| f | 0.9 | 0.9 | 0.9 |
| $\tau(\text{min}^{-1})$ | 11 | 11 | 11 |
| $i_{pb}(\text{pmole/kg})$ | 5.45 | 5.42 | 5.09 |
| $i_{lb}(\text{pmole/kg})$ | 3.09 | 3.67 | 2.85 |
| $i_{sc1ss}(\text{pmole/kg})$ | 79.95 | 84.79 | 63.84 |
| $i_{sc2ss}(\text{pmole/kg})$ | 76.35 | 77.57 | 54.29 |

The duration of each simulated scenario was set to 480 minutes and a simulation step size of 1 minute. The time of bolus insulin injection was fixed to be 1 minute before the start of each meal to mimic the meal tolerance test protocols given in [Haidar et al., 2012]. The amount of CHOs in each meal was randomized and the amount of bolus insulin was set using patient specific carbohydrate to insulin ratio using the formula given in [Dalla Man et al., 2014]. The basal insulin injection rate was fixed and set to the patient specific rate which corresponds to the rate required to maintain fasting levels. Also, the value of $u_{ii}$ was set constant to $u_{ii}=f_{cns}=1$ mg/kg/min. Simulation results were then obtained for all variables appearing in subsystem equations (1), (2), (3) and (4) for each patient.

Three sets of continuous time system matrices $A_c$, $B_c$, $C_c$ (one for each patient) were then formed using patient parameters given in Table 1 and the formulation given in (25). The continuous system matrices were then discretized using zero order hold approximation with $T_s=5$ min to obtained matrices A, B and C needed to construct the discrete time system (9) for each patient.

Figure 5:
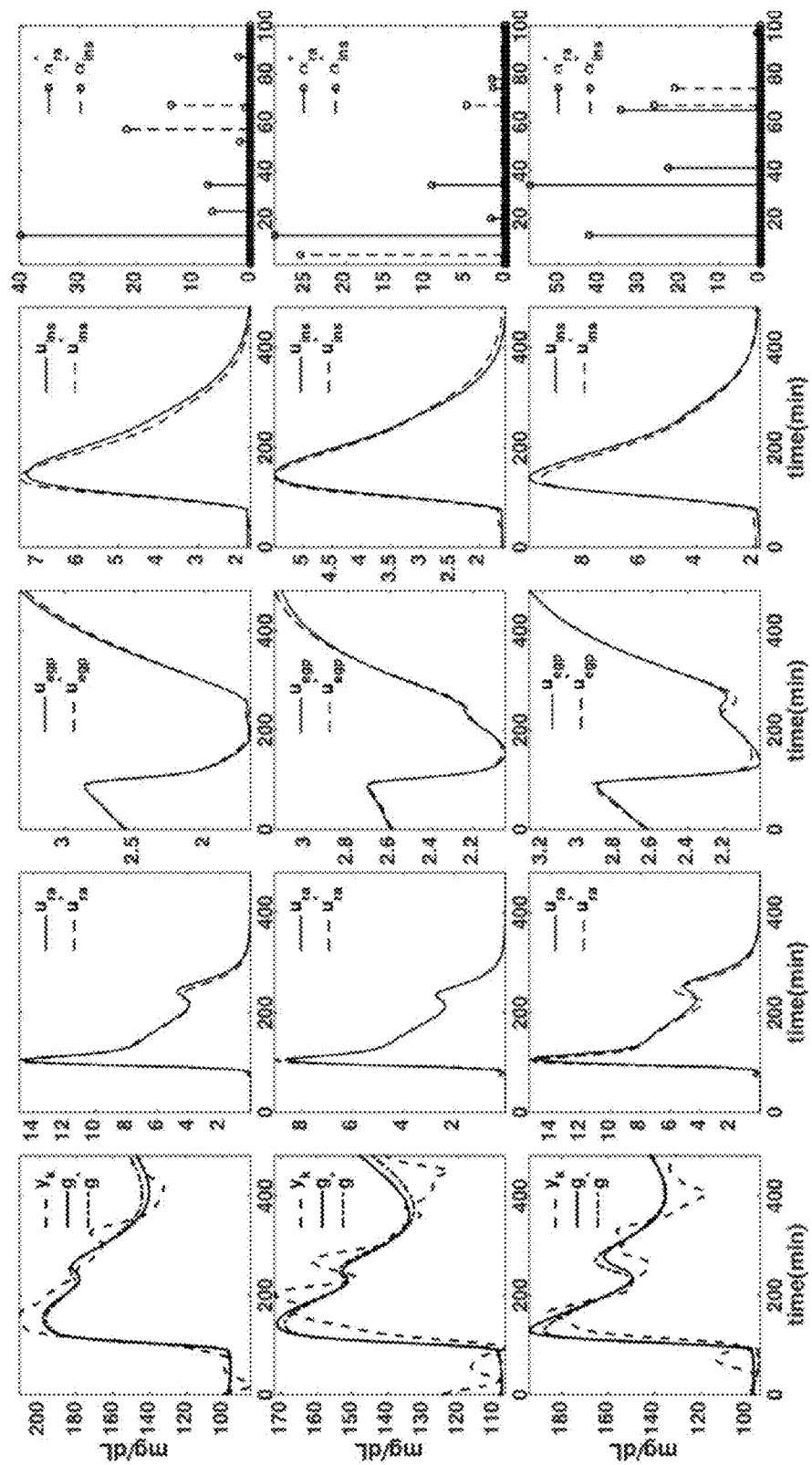
FIG. 5 is a figure showing plots for the results obtained for experiment I in the simulation examples.

For each meal and for each patient, the measurement vector sequence was constructed as $y_k = g_{sc}(kT_s) + v_k$, where $v_k \in \mathbb{R}$ is additive noise generated using a SU Johnson distribution with an autoregressive dynamic as explained in [Breton and Kovatchev, 2008]. Referring to (10), the parameters of the SU Johnson noise distribution used were set to $\tilde{\lambda}=15.96$, $\tilde{\gamma}=-0.5444$, $\tilde{\delta}=1.69$, $\tilde{\xi}=-5.47$ and the autocorrelation coefficient was set to $\tilde{\kappa}=0.7$. The initial estimate for the state was set to $\bar{x}_0 = x_0 + v_x$, where $x_0$ is the true value of the state at time zero and $v_x \in \mathbb{R}^9$ is additive normally distributed pseudo-random noise vector generated in Matlab with zero mean and covariance matrix $5 \times I_9$. Similarly, $c_{carbs} = \bar{c}_{carbs} v_{carbs}$, where $\bar{c}_{carbs}$ is the value used in the simulation experiment and $v_{carbs}$ is additive normally distributed noise with zero mean and covariance of 1. The known input sequence $\tilde{u}_k$ was set to $\tilde{u}_k = [k_{p1}, u_{cns}, u_{iir}(kT_s)]^T$ using the same bolus and basal insulin inputs used in simulation. The other parameters in (19) were set as follows: $\varepsilon_{x_0}=5$, $\lambda=0.1$, $f=0.9$. Finally, the glucose flux dictionaries $D_{ra}$ and $D_{ins}$ constructed in section 4 for the MTT conditions were used. Consequently, the minimization problem (19) was solved using Matlab CVX [Grant and Boyd, 2012] for the average adolescent, average adult and average child patient respectively for all 100 trials. FIG. 5 shows a sample of the results obtained for this simulation experiment. As it can be observed in FIG. 5, good estimation results were achieved for all glucose flux types and for all three in-silico patients despite the significant noise present in CGS measurements, the initial conditions and the meal information provided. Moreover, these results were achieved despite using the same set of glucose flux dictionaries for all patients. The discrepancy between the estimated and true glucose flux profiles can be attributed to the combined effect of measurement noise, the appropriateness of the tuning parameter $\lambda$ used and the under-representation of the glucose flux dictionaries. Estimation performance was measured using average relative root mean square error for all estimated signals given by:

$$RRMSE = \frac{1}{N_e} \sum_{i=1}^{N_e} \sqrt{\frac{1}{N \cdot X_{range}} \|X_i^* - X_i\|_2}$$

where, $X_i$ can be either $u_{ra}$, $u_{egp}$, $u_{ins}$ signals or $g$; $X_i^*$ is either $u_{ra}^*$, $u_{egp}^*$, $u_{ins}^*$ or $g^*$ the corresponding estimated signal vectors; $X_{range} = \max_i X_i - \min_i X_i$; $N_e=100$ the total number of meals under analysis and N the size of the signal vector. Table 2 provides the relative average root mean square error values obtained for the three in-silico patients under study for all the simulation runs. Note, that $g^*$ is the simulated plasma glucose profile using the estimated profiles $u_{ra}^*$, $u_{egp}^*$ and $u_{ins}^*$ and can be obtained recursively using (21). The low relative root mean square error values demonstrate good recovery of all glucose fluxes which demonstrates the potential of the technique. Good estimation results were also found for the states $x_k^*$ that were found by solving (21) and the estimated initial condition $x_0^*$ (results not shown).

TABLE 2

Average relative root mean square error performance for estimated values $u_{ra}^*$, $u_{egp}^*$, $u_{ins}^*$ and $g^*$ for 100 random simulation trials (Scenario 1)

| Patient/RRMSE | $u_{ra}^*$ | $u_{egp}^*$ | $u_{ins}^*$ | $g^*$ |
|---|---|---|---|---|
| average adolescent | 0.0347 | 0.2070 | 0.0505 | 0.0512 |
| average adult | 0.0403 | 0.2600 | 0.0527 | 0.0643 |
| average child | 0.0308 | 0.1401 | 0.0304 | 0.0415 |
| Average | 0.0353 | 0.202 | 0.0405 | 0.0523 |

Experiment II: Meal Tolerance Test Conditions with Glucose Subsystem Model Only

In this simulation experiment, three simulation trials are conducted using the UVa/Padova simulator similar to experiment 1 explained above but with imperfect knowledge of patient parameters $k_1$, $k_2$, $v_g$ and $\tau$ while using the glucose subsystem model given in (1) only. In this case, additional information is needed in the form of estimates $\bar{c}_{cir}$, $\bar{u}_{egp}(0)$, and error bounds $\varepsilon_{cir}$ and $\varepsilon_{egp}$ as described earlier. In addition, a dictionary that sparsely encodes plausible flux profiles for EGP is also needed as described earlier.

In this simulation experiment, three sets of continuous time system matrices $A_c$, $B_c$, $C_c$ (one for each patient) were then formed using patient parameters given in Table 1 and the formulation given in (25). The continuous system matrices were then discretized using zero order hold approximation with $T_s=5$ min to obtained matrices A, B and C needed to construct the discrete time system (9) for each patient as before.

Using the same simulation data results obtained earlier for experiment 1, for each meal and for each patient, the measurement vector sequence was constructed as $y_k = g_{sc}(kT_s) + v_k$, as explained in experiment 1. Similarly, the initial estimate for the state was set to $\bar{x}_0 = x_0 + v_x$ as explained earlier in experiment 1. Also, the known input sequence $\tilde{u}_k$ was set to $\tilde{u}_k = [f_{cns}]^T$, with $f_{cns}=1$. The parameters in (31) were set as follows: $\varepsilon_{x_0}=5$, $\lambda=0.1$, $f=0.9$ and $\bar{c}_{carbs}$ was set to the same value used in the simulation experiment with additional white random noise of zero mean and covariance equal to 1. An estimate of patient CIR was formed by defining $\bar{c}_{cir} = c_{cir} + v_{cir}$ where $v_{cir}$ is zero mean covariance 1 random white noise. Finally the initial value of the EGP flux was set to $\bar{u}_{egp}(0) = u_{egp}(0) + v_{egp}$, where $v_{egp}$ is zero mean covariance 1 random noise. The glucose flux dictionaries $D_{ra}$, $D_{egp}$, and $D_{ins}$ constructed in earlier in section IV for the MTT conditions are used.

Figure 6:
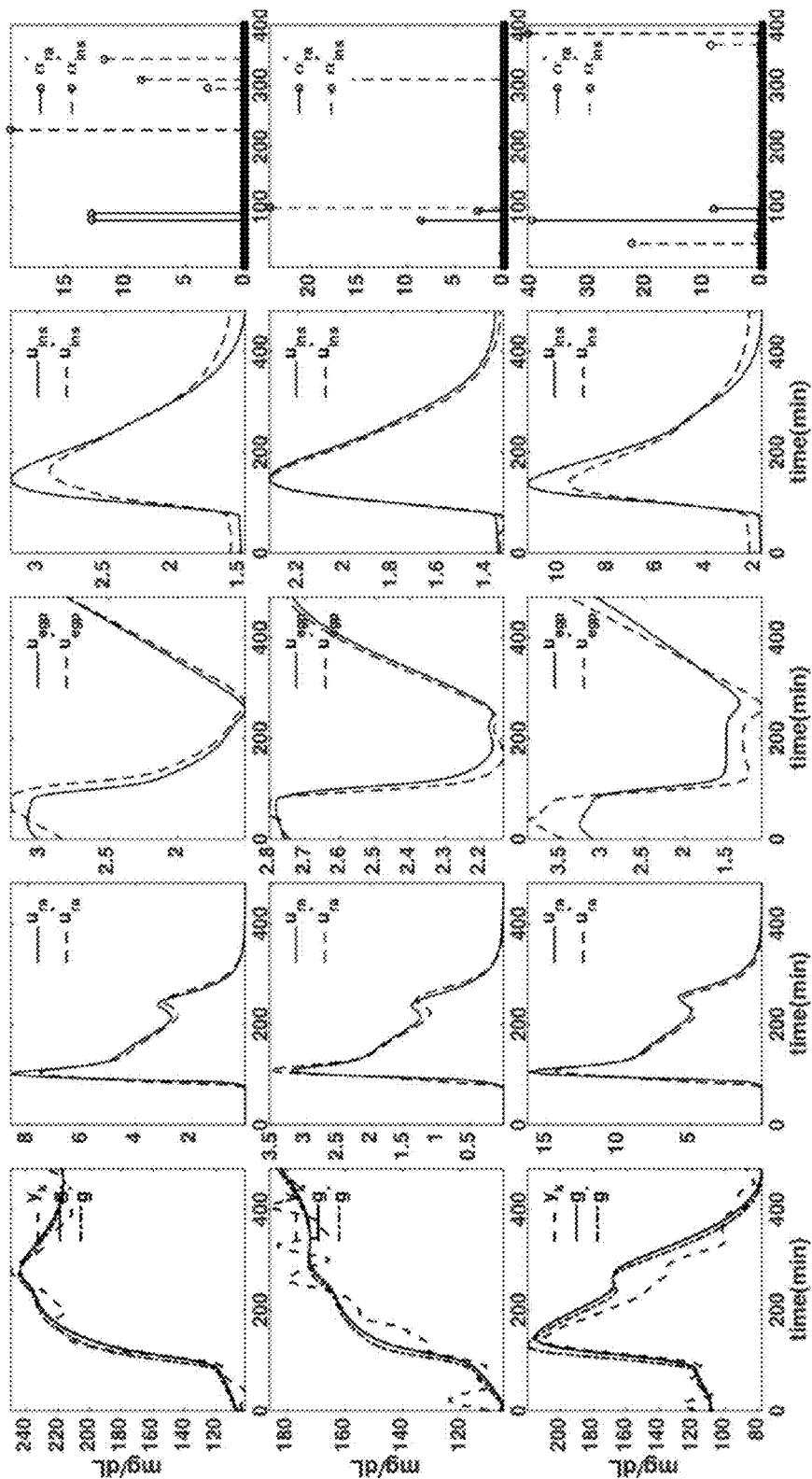
FIG. 6 is a figure showing plots for the results obtained for experiment II in the simulation examples.

The minimization problem (31) was then solved using Matlab CVX [Grant and Boyd, 2012] for the average adolescent, average adult and average child patient respectively for the single meal. FIG. 6 shows the results obtained for this simulation experiment. As can be observed in FIG. 6, near exact recovery of the glucose fluxes was achieved for all glucose flux types and for all three in-silico patients despite the significant noise present in the measurements and initial conditions as in experiment 1. Moreover, this result was achieved despite using the same set of flux dictionaries for all patients and despite no information is available regarding insulin delivery and patient model parameters relevant to the insulin subsystem models given in (2) and (3) and the endogenous glucose subsystem in (4). The discrepancy between the estimated and true glucose flux profiles can be attributed again to the combining effect of measurement noise present and the appropriateness of the tuning parameter $\lambda$ used.

Figure 7:
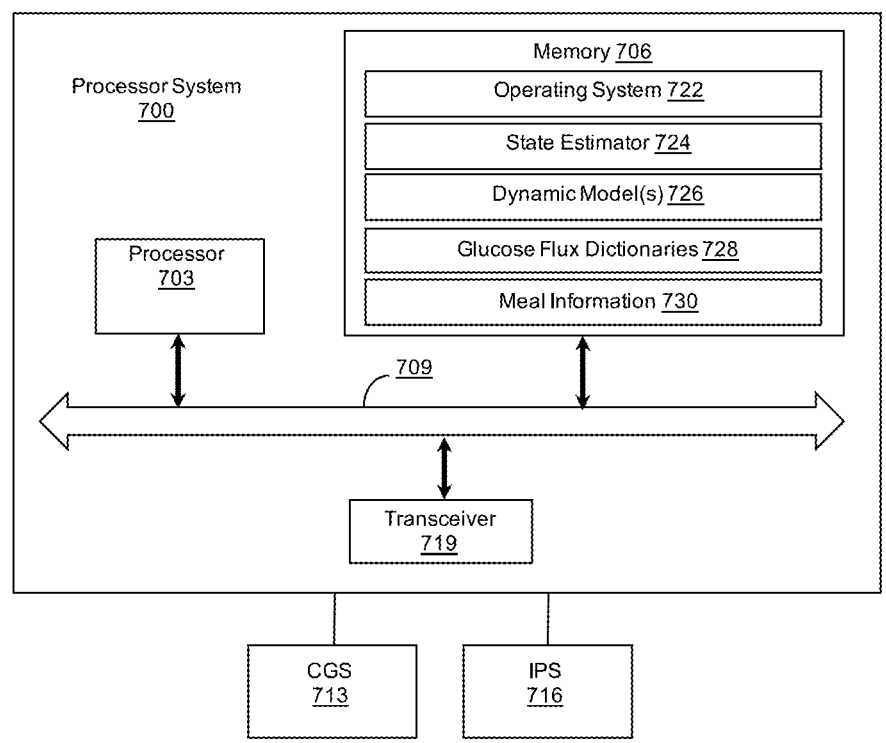
FIG. 7 is a block diagram of the present disclosure.

FIG. 7 shows one example of a system that performs various functions for continuous glucose rate of appearance measurements, endogenous glucose production measurements and glucose utilization measurements in accordance with various embodiments as set forth above. As shown, a processor system 700 is provided that includes a processor 703 and a memory 706, both of which are coupled to a local interface 709. The local interface 709 may be, for example, a data bus with an accompanying control/address bus as can be appreciated by those with ordinary skill in the art. The processor system 700 may comprise, for example, a computer system such as a server, desktop computer, laptop, mobile device (e.g., smart phone, tablet, personal digital assistant, etc.) or other system with like capability.

Coupled to the processor system 700 are various peripheral devices such as, for example, a continuous glucose sensor (CGS) 713, an insulin pump system (IPS) 716 and/or other devices as can be appreciated. The CGS 713, insulin pump system 716 can communicate with the processor system 700 via a transceiver 709 (or transmitter and/or receiver). The communications can be wired or wireless (e.g., Bluetooth, WiFi, etc.).

Stored in the memory 706 and executed by the processor 703 are various components that provide various functionality according to the various embodiments of the present disclosure. In the example embodiment shown, stored in the memory 706 is an operating system 722, a state estimator application 724, various dynamic models 726, glucose flux dictionaries 728 that encode an available database for plausible profile signals for GRA, EGP and U, meal information 730 and potentially other information associated with the glucose rate of appearance, endogenous glucose production and insulin dependent glucose utilization.

The state estimator application 724 and dynamic models 726 can be executed by the processor 703 in order to determine the glucose rate of appearance, endogenous glucose production and glucose utilization as previously described. A number of software components are stored in the memory 706 and are executable by the processor 703. In this respect, the term "executable" means a program file that is in a form coupled to the processor system 700 and various peripheral devices such as, for example, a CGS 713, an insulin pump system (IPS) 716, and/or other devices as can be appreciated. The CGS 713 and insulin pump system 716 can communicate with the processor system 700 via a transceiver 719 (or transmitter and/or receiver). The communications can be wired or wireless (e.g., Bluetooth, WiFi, etc.). Stored in the memory 706 and executed by the processor 703 are various components that provide various functionality according to the various embodiments of the present invention. In the example embodiment shown, stored in the memory 706 is an operating system 722, a state estimator application 724, various dynamic models 726, glucose flux dictionaries 728, meal information 730 and potentially other information associated with the glucose rate of appearance, endogenous glucose production and insulin dependent glucose utilization. The state estimator application 724 and dynamic models 726 can be executed by the processor 703 in order to determine the glucose rate of appearance, endogenous glucose production and insulin dependent glucose utilization as described in the preferred embodiments of the present invention. A number of software components are stored in the memory 706 and are executable by the processor 703. In this respect, the term "executable" means a program file that is in a form that can ultimately be run by the processor 703. Examples of executable programs may be, for example, a compiled program that can be translated into machine code in a format that can be loaded into a random access portion of memory 706 and run by the processor 703, or source code that may be expressed in proper format such as object code that is capable of being loaded into a random access portion of memory 706 and executed by processor 703, etc. An executable program may be stored in any portion or component of memory 706 including, for example, random access memory, read-only memory, a hard drive, compact disk (CD), floppy disk, or other memory components.

Memory 706 is defined herein as both volatile and non-volatile memory and data storage components. Volatile components are those that do not retain data values upon loss of power. Nonvolatile components are those that retain data upon a loss of power. Thus, memory 706 may comprise, for example, random access memory (RAM), read-only memory (ROM), hard disk drives, floppy disks accessed via an associated floppy disk drive, compact discs accessed via a compact disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Processor 703 may represent multiple processors and memory 706 may represent multiple memories that operate in parallel. In such a case, local interface 709 may be an appropriate network that facilitates communication between any two of the multiple processors, between any processor and any one of the memories, or between any two of the memories etc. Processor 703 may be of electrical, optical, or molecular construction, or of some other construction as can be appreciated by those with ordinary skill in the art. Operating system 722 is executed to control the allocation and usage of hardware resources such as the memory, processing time and peripheral devices in processor system 700. In this manner, operating system 722 serves as the foundation on which applications depend as is generally known by those with ordinary skill in the art. Although state estimation application 724 and dynamic models are described as being embodied in software or code executed by general purpose hardware as discussed above, as an alternative the same may also be embodied in dedicated hardware or a combination of software/general purpose hardware and dedicated hardware. If embodied in dedicated hardware, each of state estimation application 724 and dynamic models can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, programmable gate arrays (PGA), field programmable gate arrays (FPGA), microcontrollers (MC), digital signal processors (DSP) or other components, etc. Such technologies are generally well known by those skilled in the art and, consequently, are not described in detail herein. Also, where state estimation application 724, dynamic models and glucose flux dictionaries 728 may comprise software or code, each can be embodied in any computer-readable medium for use by or in connection with an instruction execution system such as, for example, a processor in a computer system or other system. In this sense, the logic may comprise, for example, statements including instructions and declarations that can be fetched from the computer readable medium and executed by the instruction execution system. In the context of the present invention, a "computer-readable medium" can be any medium that can contain, store, or maintain state estimation application 724, dynamic models and glucose flux dictionaries 730 for use by or in connection with the instruction execution system. The computer readable medium can comprise any one of many physical media such as, for example, electronic, magnetic, optical, electromagnetic, infrared, or semiconductor media. More specific examples of a suitable computer-readable medium would include, but are not limited to, magnetic tapes, magnetic floppy diskettes, magnetic hard drives, or compact discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

The invention claimed is:

1. A measurement system for measuring glucose rate of appearance, endogenous glucose production and insulin dependent glucose utilization comprising: a receiver configured to receive subcutaneous glucose concentration data from a continuous glucose sensor that is coupled to a patient, the receiver further configured to receive insulin infusion data from an insulin infusion device or from the user through an input device, the receiver further configured to receive meal information data from the user through an input device, the receiver further configured to receive information regarding the initial condition for the glucose/insulin model of the patient used; processing logic configured to determine a blood glucose and insulin concentration in the subject in response to a glucose disturbance and/or insulin infusion or a combination of both; and processing logic configured to determine an estimated glucose rate of appearance from the intestine, an estimated endogenous glucose production from the liver and an estimated insulin dependent glucose utilization in response to received subcutaneous glucose concentration data and subcutaneous insulin delivery data, initial condition data in response to the glucose disturbance and/or insulin infusion or a combination of both and the rate of glucose appearance from the intestine, rate of endogenous glucose production and rate of insulin dependent glucose utilization of the subject.

2. The measurement system for measuring glucose rate of appearance, endogenous glucose production and insulin dependent glucose utilization measurement system of claim 1 wherein the subcutaneous glucose concentration data is noisy subcutaneous glucose concentration data and insulin infusion data is noisy subcutaneous insulin infusion data.

3. The glucose rate of appearance, endogenous glucose production and insulin dependent glucose utilization measurement system of claim 2 wherein the processing logic configured to determine an estimated glucose rate of appearance from the intestine, endogenous glucose production and insulin dependent glucose utilization is further configured to determine a filtered subcutaneous glucose concentration.

4. The glucose rate of appearance, endogenous glucose production and insulin dependent glucose utilization measurement system of claim 1 wherein the glucose disturbance is a meal, an infusion of insulin, or a combination thereof.

5. The glucose rate of appearance, endogenous glucose production and insulin dependent glucose utilization measurement system of claim 1 further comprising processing logic configured to determine an estimate of patient carbohydrate to insulin ratio.

6. A method of estimating a glucose rate of appearance, endogenous glucose production and insulin dependent glucose utilization the method comprising: receiving subcutaneous glucose concentration data from a continuous glucose sensor that is coupled to a subject; receiving insulin infusion data from an insulin infusion device or from the user through an input device; receiving meal information data from a user through an input device; receiving initial condition data relevant to the glucose/insulin model of the patient; determining a blood glucose and insulin concentration in the subject in response to a glucose disturbance and/or an insulin disturbance or a combination of both, a rate of glucose appearance from the intestine of the subject, a rate of endogenous glucose production and a rate of insulin dependent glucose utilization; and determining an estimated glucose rate of appearance, endogenous glucose production and insulin dependent glucose utilization in response to received subcutaneous glucose concentration data, insulin infusion data and a determined blood glucose concentration in the subject in response to the glucose and/or insulin disturbance or a combination of both and the rate of glucose appearance from the intestine, rate of endogenous glucose production and rate of insulin dependent glucose utilization of the subject.

7. The method of estimating a glucose rate of appearance, endogenous glucose production and insulin dependent glucose utilization of claim 5 wherein the subcutaneous glucose concentration data is noisy subcutaneous glucose concentration data and the insulin infusion data is noisy subcutaneous insulin infusion data, the meal information data is noisy meal information data and the initial condition data relevant to the glucose/insulin model of the patient is noisy initial condition data.

8. The method of estimating a glucose rate of appearance, endogenous glucose production and insulin dependent glucose utilization of claim 5 wherein the step of determining an estimated glucose rate of appearance, endogenous glucose production and insulin dependent glucose utilization further comprises determining a filtered subcutaneous glucose concentration.

9. The method of estimating a glucose rate of appearance, endogenous glucose production and insulin dependent glucose utilization of claim 5 wherein the glucose disturbance is a meal, an infusion of insulin, or a combination thereof.

10. The glucose rate of appearance, endogenous glucose production and insulin dependent glucose utilization measurement system of claim 2 wherein the glucose disturbance is a meal, an infusion of insulin, or a combination thereof.

11. The glucose rate of appearance, endogenous glucose production and insulin dependent glucose utilization measurement system of claim 3 wherein the glucose disturbance is a meal, an infusion of insulin, or a combination thereof.

12. The glucose rate of appearance, endogenous glucose production and insulin dependent glucose utilization measurement system of any one of claim 2 further comprising processing logic configured to determine an estimate of patient carbohydrate to insulin ratio.

13. The glucose rate of appearance, endogenous glucose production and insulin dependent glucose utilization measurement system of claim 3 further comprising processing logic configured to determine an estimate of patient carbohydrate to insulin ratio.

14. The glucose rate of appearance, endogenous glucose production and insulin dependent glucose utilization measurement system of any one of claim 4 further comprising processing logic configured to determine an estimate of patient carbohydrate to insulin ratio.

15. The method of estimating a glucose rate of appearance, endogenous glucose production and insulin dependent glucose utilization of claim 6 wherein the glucose disturbance is a meal, an infusion of insulin, or a combination thereof.

16. The method of estimating a glucose rate of appearance, endogenous glucose production and insulin dependent glucose utilization of claim 7 wherein the glucose disturbance is a meal, an infusion of insulin, or a combination thereof.

* * * * *